United States Patent [19]

Viets

[11] 4,412,384
[45] Nov. 1, 1983

[54] HEIGHT MEASURING DEVICE HAVING LEVEL INSTRUMENT AND PLATFORM

[76] Inventor: William Viets, 849 Barth La., Kettering, Ohio 45429

[21] Appl. No.: 273,467

[22] Filed: Jun. 15, 1981

[51] Int. Cl.³ .......................... G01B 3/10; G01B 5/00
[52] U.S. Cl. ...................................... 33/169 R; 33/138
[58] Field of Search ............ 33/137, 138, 139, 169 R, 33/143 R

[56] References Cited

U.S. PATENT DOCUMENTS

| | | | |
|---|---|---|---|
| 491,733 | 2/1893 | Foster | 33/169 R |
| 652,814 | 7/1900 | Setzer | 33/138 X |
| 748,094 | 12/1903 | Parker | 33/138 |
| 823,373 | 6/1906 | Tatum | 33/138 X |
| 913,703 | 3/1909 | Darter | 33/138 X |
| 1,346,619 | 7/1920 | Weathersby | 33/376 |
| 2,728,143 | 12/1955 | Buchet | 33/138 |
| 3,336,674 | 8/1967 | Higgins et al. | 33/137 R X |

FOREIGN PATENT DOCUMENTS

| | | | |
|---|---|---|---|
| 1551242 | 11/1968 | France | 33/138 |
| 332883 | 7/1930 | United Kingdom | 33/138 |

*Primary Examiner*—Harry N. Haroian
*Attorney, Agent, or Firm*—Jacox & Meckstroth

[57] ABSTRACT

A personnel height mesuring device which includes a platform upon which a person stands. A frame is releasably attachable to the platform and is movable with respect to the platform. An extensible tape is carried by the frame and has an end portion attached to the platform. A level indicator member is carried by the frame for indicating the level condition thereof as the frame rests upon the head of the person being measured. The extended position of the tape is noted to determine the height of the person standing upon the platform.

4 Claims, 9 Drawing Figures

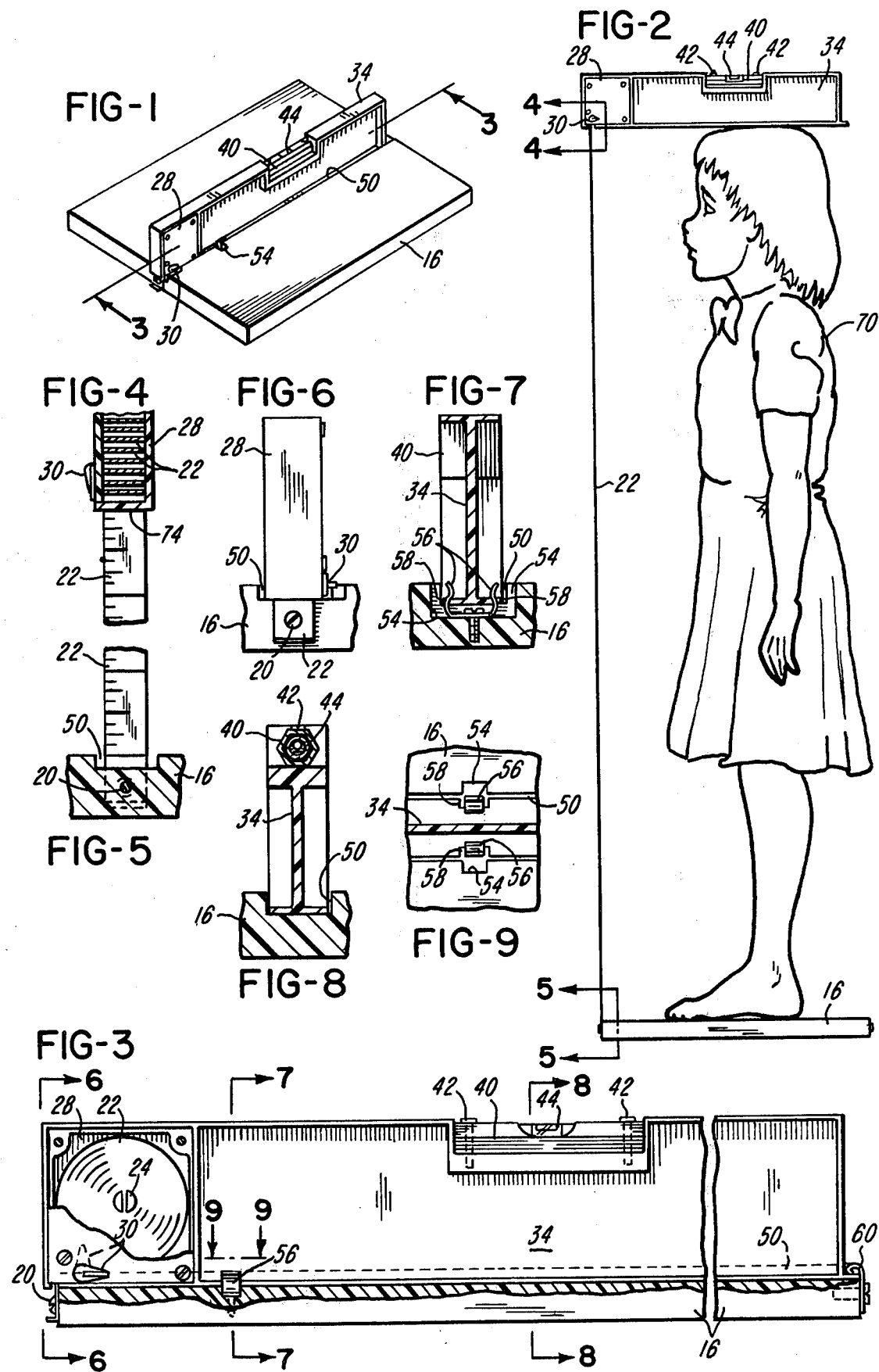

1

HEIGHT MEASURING DEVICE HAVING LEVEL INSTRUMENT AND PLATFORM

BACKGROUND OF THE INVENTION

Numerous types of devices have been created for measuring the height of a person. However, most devices which are capable of accurate height measurement are large and cumbersome and are not portable. Known portable height measuring devices are not accurate.

It is, therefore, an object of this invention to provide a height measuring device which is readily portable and which is also accurate.

Other objects and advantages of this invention reside in the construction of parts, the combination thereof, the method and production and the mode of operation, as will become more apparent from the following description.

BRIEF DESCRIPTION OF THE VIEWS OF THE DRAWING

FIG. 1 is a perspective view of a height measuring device of this invention, showing the device in its collapsed condition for carrying and/or for storage.

FIG. 2 is a side elevational view, illustrating the height measuring device of this invention in use in measuring the height of a person.

FIG. 3 is an enlarged sectional view with parts broken away, taken substantially on line 3—3 of FIG. 1.

FIG. 4 is an enlarged fragmentary sectional view, with parts broken away, taken substantially on line 4—4 of FIG. 2.

FIG. 5 is an enlarged fragmentary sectionalal view taken substantially on line 5—5 of FIG. 2.

FIG. 6 is an enlarged fragmentary elevational view taken substantially on line 6—6 of FIG. 3.

FIG. 7 is an enlarged fragmentary sectional view taken substantially on line 7—7 of FIG. 3.

FIG. 8 is an enlarged fragmentary sectional view taken substantially on line 8—8 of FIG. 3.

FIG. 9 is an enlarged fragmentary sectional view taken substantially on line 9—9 of FIG. 3.

DETAILED DESCRIPTION OF THE INVENTION

A height measuring device of this invention comprises a platform 16 which is adapted to support a person for measurement of the height of the person. Attached to the platform 16 by any suitable means, such as by means of a screw 20, is one end of a measuring tape 22. The tape 22 is wound upon a shaft 24 within a tape houing 28. Preferably the tape 22 is of the spring powered return type. A pivotal lever 30, carried by the housing 28, operates a locking mechanism, not shown, for locking the extended position of the tape 22 with respect to the shaft 24 and with respect to the tape housing 28.

The tape housing 28 is within and a part of an elongate frame 34. Intermediate the ends of the frame 34 is a spirit type level member 40 which is attached to the frame 34 by means of screws 42. The spirit type level member 40 includes a bubble tube 44.

The platform 16 has an elongate recess 50 which extends the length thereof. The recess 50 is adapted to receive the lower portion of the frame 34. Mounted in the platform 16 within notches 54 thereof adjacent the recess 50 are opposed resilient clips 56, best shown in FIGS. 3, 7, and 9, which are adapted to engage notched portions 58 in the lower part of the frame 34 to retain the lower part of the frame 34 within the recess 50, as illustrated in FIGS. 1, 3, 6, 7, 8, and 9. At the end of the platform 16, opposite the screw 20, is a resilient clip 60 which assists in retaining the lower part of the frame 34 within the recess 50.

When it is desired to measure the height of a person, such as a person 70, shown in FIG. 2, the frame 34 is released from the clips 56 and removed from the recess 50. The person 70 stands on the platform 16. The frame 34 with the tape housing 28 attached thereto is lifted from the platform 16, as the tape 22 is extended from the tape housing 28. The frame 34 with the tape housing 28 is moved to a position above the head of the person 70. The frame 34 is rested upon the head of the person 70. The frame 34 is oriented so that the bubble in the bubble tube 44 in the level member 40 indicates that the frame 34 is level upon the head of the person 70. Then, preferably the lever 30 is pivotally moved to operate the lock in the tape housing 28 to secure the extended position of the tape 22. Then, indicia 74 on the tape 22 in alignment with the lower surface of the frame 34 are noted to determine the length of the extended portion of the tape 22 and thus determine the height of the person 70.

After the height of the person 70 is measured, the person 70 steps off of the platform 16. The lever 30 is pivotally moved to release the lock in the tape housing 28, to permit the tape 22 to wind upon the shaft 24. The lower part of the frame 34 is again positioned within the recess 50 of the platform 16, and the resilient clips 56 again retain the lower portion of the frame 34 within the recess 50 of the platform 16. Thus, the platform 16, the frame 34 and the tape housing 28 with the tape 22 therewithin are a compact unit for carrying thereof and/or for storage thereof.

Although the preferred embodiment of a height measuring device of this invention has been described, it will be understood that within the purview of this invention various changes may be made in the form, details, proportion and arrangement of parts, the combination thereof, and the mode of operation, which generally stated consist in a height measuring device within the scope of the appended claims.

The invention having thus been described, the following is claimed.

1. In a device for measuring the height of a person and including a platform, an elongate support member having a lower portion, the platform and the support member being relatively movable, a coiled measuring tape having units of measurements thereupon, the coiled measuring tape being carried by the support member, the measuring tape having an end portion attached to the platform, successive portions of the tape being uncoiled and extendible from the lower portion of the support member as the support member is elevated from the platform when a person whose height is to be measured stands on the platform, a level indicator member carried by the support member, the support member being positionable upon the head of the person whose height is to be measured as the support member is oriented to a level position by use of the level indicator member, and the height of the person being noted by observing the indicia upon the measuring tape adjacent the support member, the improvement wherein the platform has a slot for receiving the lower portion of the support member, resilient clip means mounted within the slot and engageable with the lower portion of the support member for releasably attaching the support member to the platform, the clip means being completely recessed within the slot of the platform to provide for unobstructed standing on the platform by the persone whose height is being measured, and to provide a compact unit for carrying and/or storage of the device when the device is not in use for measuring.

2. A device for measuring height of a person comprising: a platform, a frame, the frame being movable with respect to the platform, a tape, means joining the tape to the frame for movement therewith, the tape having an end portion, means attaching the end portion of the tape to the platform, the end portion of the tape and successive portions of the tape being extendible from the frame with movement of the frame from the platform, a level indicator member carried by the frame, the tape being extendible from the frame as a person stands upon the platform and as the frame is moved to a position above the head of the person, the frame resting upon the head of the person as the level indicator member indicates a level position of the frame, the extended position of the tape from the frame being noted as the measurement of the height of the person, means releasably attaching the frame to the platform.

3. A device for measuring the height of a person comprising: a platform, a support member, the platform and the support member being relatively movable, a coiled measuring tape having indicia thereupon, the coiled measuring tape being carried by the support member, the measuring tape having an end portion attached to the platform, successive portions of the tape being uncoiled and extendible from the support member as the support member is moved from the platform, as a person whose height is to be measured stands on the platform, a level indicator member carried by the support member, the support member being positionable upon the head of the person whose height is to be measured as the support member is oriented to a level position by use of a level indicator member, the height of the person being noted by observing the indicia upon the measuring tape adjacent the support member, the support member comprising a frame, the platform having a recess into which a portion of the frame is positionable, and including resilient clip members adjacent the recess and engageable with the frame to releasably retain the frame with respect to the platform.

4. A device for measuring the height of a person comprising: a platform, a support member, the platform and the support member being relatively movable, a coiled measuring tape having indicia thereupon, the coiled measuring tape being carried by the support member, the measuring tape having an end portion attached to the platform, successive portions of the tape being uncoiled and extendible from the support member as the support member is moved from the platform, as a person whose height is to be measured stands on the platform, a level indicator member carried by the support member, the support member being positionable upon the head of the person whose height is to be measured as the support member is oriented to a level position by use of the level indicator member, the height of the person being noted by observing the indicia upon the measuring tape adjacent the support member, resilient clip members attached to the platform and engageable with the frame to releasably retain the frame with respect to the platform.

* * * * *